United States Patent [19]

Portelli et al.

[11] 4,188,402

[45] Feb. 12, 1980

[54] DERIVATIVES OF THE D-THREO-1-PHENYL-2-TRI-FLUOROACETAMIDO-1,3-PROPANDEDIOL

[75] Inventors: Mario Portelli, Vicenza; Davide DellaBella, Milan; Giuseppe Cervato, Vicenza; Gianfranco Marca, Vimercate, all of Italy

[73] Assignee: Clesa S.p.A., Vicenza, Italy

[21] Appl. No.: 822,258

[22] Filed: Aug. 5, 1977

[51] Int. Cl.² ............................................. A61K 31/165
[52] U.S. Cl. .................................. 424/324; 260/562 R
[58] Field of Search ........................... 560/33, 115, 25; 260/562 R, 562 A, 562 B, 562 S; 424/324

[56] References Cited

U.S. PATENT DOCUMENTS

| 2,759,927 | 8/1956 | Suter | 260/562 |
| 3,100,781 | 8/1963 | Concilio | 260/482 |
| 3,190,910 | 6/1965 | Nicolaides | 260/482 |
| 3,542,854 | 11/1970 | Teotino | 260/482 |

FOREIGN PATENT DOCUMENTS

| 1221239 | 7/1966 | Fed. Rep. of Germany | 260/482 |
| 1488658 | 7/1967 | France | 260/425 |

OTHER PUBLICATIONS

Feitelson et al., "J. Pharm. Pharmacol, vol. 3 (1951), pp. 149-159.
Kanazawa et al., Chem. Abst. vol. 74, p. 86185b (1971).
Knanzawa et al., Chem. Abst. vol. 74, p. 135343n (1971).
Tsutsumi et al., Chem. Abst. vol. 74, p. 138955z.

Primary Examiner—Werren B. Lone
Attorney, Agent, or Firm—Joseph W. Molasky

[57] ABSTRACT

A novel class of D-Threo-1-phenyl-1-trifluoroacetamido-1, 3-propanediols wherein the benzene ring is substituted in the para-position by methylmercapto or methanesulphonyl and the hydroxy moiety at position 3 of the prepanediol is acylated to afford alkanoyloxy, halo-alkanoyloxy or aminoalkanoyloxy.

The instant products are prepared: (1) by treating a D-threo-1-(p-methanesulphonylphenyl)-2-amino-1,3-propanediol or a D-threo-1-(p-methylmercaptophenyl)-2-amino-1,3-propanediol with trifluoroacetic acid or with an ester derivative thereof; (2) by oxidation of the mercapto moiety in a D-threo-1-(p-methylmercaptophenyl)-2-trifluoroacetamido-1, 3-propanediol to afford the corresponding 1-(p-methanesulphonyl) derivative; or (3) by esterification of the 3-hydroxy moiety in a D-threo-1-phenyl-2-trifluoroacetamido-1, 3-propanediol precursor.

9 Claims, No Drawings

DERIVATIVES OF THE D-THREO-1-PHENYL-2-TRIFLUOROACETAMIDO-1,3-PROPANDEDIOL

This invention relates to novel derivatives of D-threo-1-phenyl-1-trifluoroacetamido-1,3-propanediol, to a method for their preparation and to pharmaceutical compositions comprising same.

The instant products are D-threo compounds of the general formula:

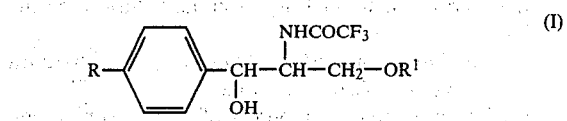

wherein R is methylmercapto or methanesulphonyl and $R^1$ is hydrogen, alkanoyl, halo-lower alkanoyl or amino-lower alkanoyl.

This invention also includes the non-toxic pharmacologically acceptable acid addition salts of those compounds of the formula I wherein $R^1$ represents an amino-lower alkanoyl moiety, such as aminoacetyl. Any acid which will form acid addition salts with the amino group of said amino-lower alkanoyl moiety and whose pharmacological properties will not cause an adverse physiological effect are considered as being within the scope of this invention. Suitable acids include, for example, mineral acids such as hydrochloric acid, hydrobromic acid or sulfuric acid and the like, or organic acids such as methanesulphonic acid, acetic acid, tartaric acid, lactic acid, citric acid, malic acid or salicylic acid and the like.

The products of this invention possess a wide spectrum of antibiotic activity and certain compounds such as those of formula I wherein $R^1$ is halo-lower alkanoyloxy, have utility as intermediates in preparign the pharmacologically active amino-lower alkanoyloxy analog.

A preferred embodiment of this invention comprises those D-threo-1-phenyl-1-trifluoroacetamido-1,3-propanediol derivatives of Formula I wherein R is methylmercapto or methanesulphonyl and $R^1$ is hydrogen, alkanoyl of 15-17 carbon atoms, halo-lower alkanoyl or amino-lower alkanoyl; with the proviso that when $R^1$ is alkanoyl, halo-lower alkanoyl or amino-lower alkanoyl, R is methanesulphonyl.

Still another embodiment comprises those D-threo-1-phenyl-2-trifluoroacetamido-1,3-propanediol derivatives of Formula I wherein R is methylmercapto or methanesulphonyl and $R^1$ is hydrogen, alkanoyl of 15-17 carbon atoms, haloacetyl or aminoacetyl; with the proviso that when $R^1$ is alkanoyl of 15-17 carbon atoms, haloacetyl or aminoacetyl, R is methanesulphonyl.

An especially preferred embodiment comprises those products of Formula I wherein $R^1$ is hydrogen, alkanoyl of 15-17 carbon atoms or aminoacetyl; with the proviso that when $R^1$ is alkanoyl of 15-17 carbon atoms or aminoacetyl, R is methanesulphonyl.

The products (I) of this invention are conveniently prepared: (1) by treating a D-threo-1-(p-methanesulphonylphenyl)-2-amino-1,3-propanediol or a D-threo-1-(p-methylmercaptophenyl)-2-amino-1,3-propanediol with trifluoroacetic acid or with an ester derivative thereof; (2) by oxidation of the mercapto moiety in a D-threo-1-(p-methylmercaptophenyl)-2-trifluoroacetamido-1,3-propanediol to afford the corresponding 1-(p-methanesulphonyl) derivative; or (3) by esterification of the 3-hydroxy moiety in a D-threo-1-phenyl-2-trifluoroacetamido-1,3-propanediol precursor.

The amidation method of this invention consists essentially of treating a compound of the formula:

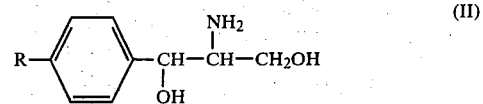

wherein R is as defined above, with trifluoroacetic acid, in the presence of a suitable condensing agent, or with a derivative of trifluoroacetic acid.

The condensing agents which are preferably used in the reaction of compound (II) with trifluoroacetic acid per se are dicarboniimides such as dicyclohexylcarbodiimide.

The derivatives of trifluoroacetic acid which may be used in this reaction are, for example, the ester, acid halide, anhydride or azide derivatives. Preferably, the methyl ester of trifluoroacetic acid in the presence of an inert organic solvent such as methyl alcohol is employed.

The oxidation method for preparing those products of Formula I wherein R is methanesulphonyl ($CH_3SO_2$-) consists of treating a D-threo-1-(p-methylmercaptophenyl)-2-amino-1-3-propanediol precursor with an oxidizing agent. For example, the product of Formula I wherein R is methanesulphonyl and $R^1$ is hydrogen, are obtained by treating a D-(-)threo-1-(p-methylmercaptophenyl)-2-amino-1,3-propanediol of the formula:

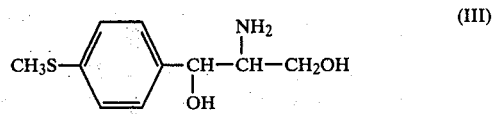

with an oxidizing agent. Suitable oxidizing agents include compounds containing a peroxidic bond as, for example, hydrogen peroxide, peracids, ammonium persulphate or potassium persulphate. Preferably, hydrogen peroxide is employed.

Also, the following compounds:

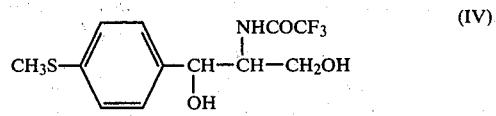

obtained as above described, can be oxidized to the corresponding p-methanesulphonyl compound by using the peroxidic-type oxidizing agents described above.

Those compounds of Formula I wherein $R^1$ is hydrogen and R is methanesulphonyl can be transformed into the corresponding esters by the following method.

This esterification method, wherein $R^1$ is an aliphatic acid radical of 15-17 carbon atoms, can be carried out by treating D-(+)-threo-1-(p-methanesulphonylphenyl)-2-trifluoroacetamido-1,3-propanediol with a free aliphatic acid or with an active derivative thereof preferably selected from the group consisting of a chloride, bromide or anhydride derivative, under critical esterification conditions so that the reaction proceeds only at the hydroxy moiety in position 3 of the propanediol while the hydroxy in the 1-position remains unchanged.

These critical esterification conditions include the use of a slight excess of the free aliphatic acid or active derivative over the stoichiometric amount, the use of an inert organic solvent and the presence of a base such as alkaline metal or alkaline earth metal hydroxide or bicarbonate, pyridine, trialkylamine, N-alkyl-aniline or N-N-dialkyl-anilines, at a temperature between 10 and 50° C.

Preferably, the chloride of the desired aliphatic acid is reacted in a suitable inert organic solvent, in the presence of pyridine. The esters thus obtained, are water-insoluble and can be separated from the reaction solution by mixing with water and crystallization from a suitable solvent.

The preparation of those esters of Formula I wherein $R^1$ is an aminoalkanoyl radical is carried out by condensing an aminoalkanoic acid such as glycine or a derivative thereof, preferably, a mixed anhydride the amino group of which is present in protected form, with D-(+)-threo-1-(p-methanesulphonylphenyl)-2-trifluoroacetamido-1,3-propanediol. There is thus obtained the corresponding amino-acetoxy derivative from which the desired ester of the amino acetic acid is obtained by cleaving off the protecting group.

As condensing agents for the reaction between the glycine and D-(+)-threo-1-(p-methanesulphonylphenyl)-2-trifluoroacetamido-1,3-propanediol, carbodiimides can be employed, preferably, dicyclohexyl-carbodiimide.

Alternatively, the ester of an aminoalkanoic acid can be prepared in two steps by first treating the D-(+)-threo-1-(p-methanesulphonylphenyl)-2-trifluoroacetamido-1, 3-propanediol with a chloroalkanoic acid halide such as chloroacetyl chloride, followed by salification of the product thus obtained with hexamethylenetetramine and by hydrolysing the resultant hexamethylenetetramine salt with a strong mineral acid, preferably, hydrochloric acid. The resulting ester is water soluble.

The ester of the aminoalkanoic acid reactant as, for example, the aminoacetic acid reactant, can be transformed into an acid addition salt by treatment with an acid which corresponds to the desired salt according to known methods.

The products of this invention have been studied to evaluate both their toxicity characteristics as well as the intensity of their antibiotic activity.

In the following Tables, which report on pharmacological studies, the compounds of this invention are referred to by abbreviation. The abbreviations are as follows:

Z 2100=D-(+)-threo-1-(p-methanesulphonylphenyl)-2-trifluoroacetamido-1,3-propanediol Z 2109=D-(−)-threo-1-(p-methylmercaptophenyl)-2-trifluoroacetamido-1,3-propanediol Z 2112=D-(+)-threo-1-(p-methanesulphonylphenyl)-2-trifluoroacetamido-3-palmitoyloxy-1-propanol Z 2117=D-(+)-threo-1-(p-methanesulphonylphenyl)-2-trifluoroacetamido-3-aminoacetoxy-1-propanol The determination of $LD_{50}$ values in the mouse by using oral and subcutaneous administration indicates that the instant compounds are very well tolerated (Table 1).

The observation of the animals was prolonged beyond one week from the administration and no adverse effects were evidenced.

Insofar as the study of the antibacterial activity spectrum is concerned, this was performed by using the method of agar dilutions in a double series. The minimum inhibitory concentration (MIC) was performed against grampositive and gram-negative microorganisms as well as Proteus.

The two derivatives having the alcoholic function esterified (Z 2112 and Z 2117 respectively) are quickly hydrolyzed in the animal organism and show the same activity as Z 2100.

The obtained results of the determination carried out in vitro have been listed in Table 2.

Furthermore, the compounds of the present invention show a certain bacterial activity, both "in vitro" and in the presence of rabbit serum, in respect of some microorganism strains resistant against thiamphenicol (ie., D-(+)-threo-1-(4-methanesulphonylphenyl)-1,3-propanediol; see Merck Index Ninth Edition, page 9034) as it appears from the following results:

|  | Thiamphenicol (MIC mcg/ml) | Z 2100 |
|---|---|---|
| *Streptococcus faecalis Z 61 | 160 | 80 |
| *Streptococcus faecalis Z 20 | 160 | 40 |
| *Staphylococcus albus 1238 | 160 | 40 |
| *Staphylococcus aureus 4180 | 160 | 40 |
| **Pseudomonas aeruginosa 50541 | 160 | 80 |
| **Streptococcus faecalis | 320 | 80 |

\* = Tests "in vitro";
\*\* = tests carried out in culture broth, in the presence of rabbit serum.

The study of the antibiotic activity of the derivatives of the present invention was completed by the determination of $PD_{50}$ in experimental infections from multocide NCTC 10722 Pasteurella induced in the mouse by intraperitoneal inoculation of a bacterial amount equal to about 100 times the lethal amount at 50%. The determination of $PD_{50}$ relating to the examined derivatives has been carried out according to the method of Spearman-Karber (L. Cavalli-Sforza "Analisi statistica per medici e biologi e analisi del dosaggio biologico"—Ed. Universitarie Boringhieri—Torino—1961, pages 173-175).

The results for the tests conducted in vivo are listed in Table 3.

TABLE 1

|  | Administration | |
|---|---|---|
| Compound | per os (mg/kg) | subcutaneous (mg/kg) |
| Z 2100 | 5000 | 5000 |
| Z 2109 | 5000 | not determined |
| Z 2112 | 5000 | not determined |
| Z 2117 | 5000 | 5000 |

TABLE 2

|  | MIC (mcg/ml) | |
|---|---|---|
| ORGANISM TEST | Z 2100 | Z 2109 |
| S. aureus Oxford | 16 | 32 |
| Proteus morgani N 520 | 8 | 4 |
| Salmonelli Typhi M-VI | 32 | 64 |
| E. Coli $K_{12}$ | 64 | 16 |
| Strep. faecalis ATCC 10541 | 8 | 32 |
| Past. multocide NCTC 10722 | 2 | 4 |
| Shighelli Boydii 4 | 8 | 32 |

TABLE 2-continued

| ORGANISM TEST | Z 2100 | MIC (mcg/ml) Z 2109 |
|---|---|---|
| Strep. agalactiae 4 b | 16 | 64 |

TABLE 3

| Compound | Administration | Treatment time (day) | PD$_{50}$ mg/kg |
|---|---|---|---|
| Z 2100 | per os | 5 | 19 |
| Z 2109 | per os | 5 | 16.6 |
| Z 2112 | per os | 5 | 21 |
| Z 2117 | subcutaneous | 5 | 14.3 |

The therapeutic compositions of this invention contain the active compounds of Formula I in mixture with a suitable excipient with functions as a carrier.

This carrier can be an inorganic or inert organic material and comprises water, gelatine, gum arabic, lactose, starch, magnesium stearate, talc, vegetable oils, polyalkylene glycols, etc.

The preparation can be made up in a solid form as, for example, as tablets, suppositories or capsules or in a liquid form as, for example, in solution, suspension or as an emulsion.

The pharmaceutical preparations may be sterilized and may contain adjuvants such as preservatives, stablizers, wetting agents, emulsifiers, salts for varying the osmotic pressure or buffers. The administration of said compositions may be oral, rectal or parenteral.

Illustrated below are typical pharmaceutical preparations:

| Preparation A: Gelatine capsule for oral administration | |
|---|---|
| D-(+)-threo-1-(p-methanesulphonylphenyl)-2-trifluoroacetamido-1,3-propanediol | 250 mg |
| Lactose | 50 mg |
| Talc | 5 mg |
| Magnesium stearate | 5 mg |

| Preparation B: Vial for parenteral administration | |
|---|---|
| Lyophilised D-(+)threo-1-(p-methanesulphonylphenyl)-2-trifluoroacetamido-1,3-propanediol | 500 mg |
| Solvent vial (physiological solution) sodium chloride | 45 mg |
| Ready-for-use-injection water q.s. | 5 ml |

This invention will now be described by reference to specific examples. However, it is to be understood that these examples are illustrative only and are not limitative. Therefore, any substitution of equivalent materials or modifications in the reaction conditions is considered as being within the scope of this invention and not a departure therefrom.

Embodiments

The process of this invention will be evident from the following Examples.

EXAMPLE 1

D-(+)-Threo-1-(p-Methanesulphonylphenyl)-2-Trifluoroacetamido-1,3-Propanediol

D-(−)-threo-1 -(p-methanesulphonylphenyl)-2-amino-1,3-propanediol (15 g., 0.0612 mol), methyl alcohol (45 ml.) and methyl trifluoroacetic ester (12.7 g., 0.0992 mol) were refluxed for four hours. The solution was evaporated under vacuum and the resulting residue was crystallized from aqueous ethyl alcohol (50% V/V).

There was thus obtained 13 g of D-(+)-threo-1-(p-methanesulphonylphenyl)-2-trifluoroacetamico-1,3-propanediol, m.p. 180°–181° C.; $[\alpha]_D^{20} = +7.7°$ (1% MeOH).

EXAMPLE 2

D-(−)-Threo-1-(p-Methylmercaptophenyl)-2-Trifluoroacetamido-1,3-Propanediol

D-(−)-threo-1-(p-methylmercaptophenyl)-2-amino-1,3-propanediol (50 g., 0.234 mol), methyl alcohol (150 ml.) and methyl trifluoroacetic ester (45 g., 0.351 mol) were refluxed for four hours.

The solution was evaporated under vacuum and the resulting residue was crystallized from aqueous ethyl alcohol (50% V/V).

There was thus obtained 52.3 g of D-(−)-threo-1-(p-methylmercaptophenyl)-2-trifluoroacetamido-1,3-propanediol, m.p. =117°–118° C.; $[\alpha]_D^{20} = -7.15°$ (1% MeOH).

EXAMPLE 3

D-(+)-Threo-1-(p-Methanesulphonylphenyl)-2-Trifluoroacetamido-1,3-Propanediol

D-(−)-Threo-1-(p-methylmercaptophenyl)-2-trifluoroacetamido-1, 3-propanediol (20 g., 0.0647 mol) was added slowly to a solution of hydrogen peroxide (21.1 g., 130 vol.) at 40° C.

Following this addition the mixture was maintained at 40° C. for 30 minutes and then acetic anhydride (21.7 g., 0.211 mol) was added at 40° C.

After maintaining the resultant mixture at 40° C. it was cooled to −10° C. and the resulting precipitate was filtered off, washed with icy water and dried to afford 15.5 g. of D-(+)-threo-1-(p-methanesulphonylphenyl)-2-trifluoroacetamido-1,3-propanediol, m.p. 179–180° C.

The product crystallized from aqueous ethyl alcohol solution (50% V/V) had a m.p. of 180°–181° C.; $[\alpha]_D^{20} = +7.7°$ C. (1% MeOH).

EXAMPLE 4

D-(+)-Threo-1-(p-Methanesulphonyl)-2-Trifluoroacetamido-3-chloroacetoxy-1-Propanol D-(+)-Threo-1-(p-methanesulphonylphenyl)-2-trifluoroacetamido1,3-propanediol (19.2 g., 0.0562 mol) was dissolved in dimethylformamide (22.5 ml.) containing pyridine (4.52 g., 0.0569 mol).

The solution was cooled to 0° C. and monochloroacetyl-chloride (6.42 g., 0.0569 mol) was added slowly with stirring.

Following the addition of monochloroacetylchloride the solution was stirred for one hour at 0° C. and it was then poured, with stirring, into a mixture of ice and water.

The resulting precipitate was precipitated, filtered and dried to aford 19.8 of crude D-(+)-threo-1-(p-methanesulphonylphenyl)-2-trifluoroacetamide-3-chloroacetoxy-1-propanol. This product was crystallized from ethyl alcohol to afford a purified product having a melting point of 168°–169° C. $[\alpha]_D^{20} = +10.4\%$ (1% MeOH).

EXAMPLE 5.

D-(+)-Threo-1-(p-Methanesulphonylphenyl)-2-Trifluoracetamido-3-Aminoacetoxy-1-Propanol Hydrochloride.

D-(+)-threo-1-(p-methanesulphonylphenyl)-2-trifluoroacetamido-3-chloroacetoxy-1-propanol (9.0 g., 0.0215 mol), acetontrile (36.5 ml.) and hexamethylenetetramine (3.02 g., 0.0215 mol) were stirred for two hours at 40°–45° C. and then left to stay overnight at room temperature. The mixture was then evaporated to dryness under vacuum and to this residue was added with stirring at 20° C. a solution of ethyl alcohol (27.5 ml.) containing concentrated hydrochloric acid (5.5 ml.).

The resulting mixture was left overnight with stirring at 30° C. and then was evaporated to dryness under vacuum.

The residue thus obtained was treated with dimethylformamide (20 ml.) and the clear solution was poured into dichloromethane (150 ml.). D-(+)-threo-1-(p-methanesulphonylphenyl)-2-trifluoroacetamido-3-aminoacetoxy-1-propanol hydrochloride (4.2 g.) was thus precipitated and this produce was crystallized from ethyl alcohol to afford a purified produce having a melting point of 190°–191° C.; $[\alpha]_D^{20} = +20.5$ (1% MeOH).

EXAMPLE 6

D-(+)-Threo-1-(p-Methanesulphonylphenyl)-2-Trifluoroacetamido-3-Palmitoyloxy-1-Propanol D-(+)-Threo-1-(p-methanesulphonylphenyl)-2-trifluoroacetamido-1, 3-propanol (9.6 g., 0.0281 mol) was dissolved in dimethylformamide (13.5 ml) containing pyridine (2.66 g., 0.0336 ml.).

Palmitoyl chloride (8.5 g., 0.0309 mol) was added slowly to the resulting solution with stirring at 10°–15° C. The solution was then heated to 35°–40° C. and was left stirring for 30 minutes.

After this period, water (60 ml.) was poured into the solution while the stirring was maintained and the mixture was cooled at 0° C. There was thus obtained a precipitate of D-(+)-threo-1-(p-methanesulphonylphenyl)-2-trifluoroacetamido-3-palmitoyloxy-1-propanol which, after filtration, weighed 15.25 g.

This product was purified by crystalization from toluene and by successive washings with petroleum ether to afford D-(+)-threo-1-(p-methanesulphonylphenyl)-2-trifuloroacetamido-3-palmitoyloxy-1-propanol having a melting point of 98°–100° C.; $[\alpha]_D^{20} = +13°$ (1% ethyl alcohol).

It should be understood that although this invention has been described with reference to particular embodiments, changes and modifications may be made within the intended scope of the following claims.

What is claimed is:

1. A D-threo compound of the formula:

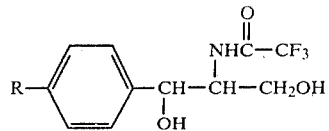

wherein R is methylmercapto or methanesulphonyl; and the non-toxic pharmacologically acceptable acid addition salts thereof.

2. The compound according to claim 1 which is D-(+)-threo-1-(p-methanesulphonylphenyl)-2-trifluoroacetamido-1,3-propanediol.

3. The compound according to claim 1 which is D-(−)-threo-1-(p-methylmercaptophenyl)-2-trifluoroacetamido-1,3-propanediol.

4. A pharmacological composition posessing antibiotic activity, which comprises as the active ingredient a D-threo-compound of the formula:

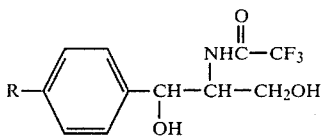

wherein R is methylmercapto or methanesulphonyl; or a non-toxic pharmacologically acceptable acid addition salt thereof, in combination with a pharmacologically acceptable carrier.

5. The composition of claim 4 wherein the active ingredient is D-(+)-threo-1-(p-methanesulphonylphenyl)-2-trifluoroacetamido-1,3-propanediol; or a non-toxic pharmacologically acceptable acid addition salt thereof, in combination with a pharmacologically acceptable carrier.

6. The composition of claim 4 wherein the active ingredient is D-(−)-threo-1-(p-methylmercaptophenyl)-2-trifluoroacetamido-1,3-propanediol; or a non-toxic pharmacologically acceptable acid addition salt thereof, in combination with a pharmacologically acceptable carrier.

7. A method of treating bacterial infection, which comprises the oral, rectal or parenteral administration of an effective amount of a D-threo compound of the formula as the active ingredient;

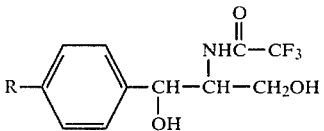

wherein R is methylmercapto or methanesulphonyl; or a non-toxic pharmacologically acceptable acid addition salt thereof.

8. The method according to claim 7 wherein the active ingredient is D-(+)-threo-1-(p-methanesulphonylphenyl)-2-trifluoroacetamido-1,3-propanediol; or a non-toxic pharmacologically acceptable acid addition salt thereof.

9. The method according to claim 7 wherein the active ingredient is D-(−)-threo-1(p-methylmercaptophenyl)-2-trifluoroacetamido-1,3-propanediol; or a non-toxic pharmacologically acceptable acid addition salt thereof.

* * * * *